United States Patent [19]
Brun et al.

[11] 3,930,990
[45] *Jan. 6, 1976

[54] PROCESS FOR SEPARATING HYDROCARBONS

[75] Inventors: Jean-Pierre Brun, Orsay; Gerard Bulvestre, Mandres-les-Roses; Michel Guillou, Creteil; Pierre Thirion, Bougival; Rene Pautrat, Le Mans, all of France

[73] Assignee: Agence Nationale de Valorisation de la Recherche (ANVAR), Hauts-de-Seine, France

[ * ] Notice: The portion of the term of this patent subsequent to June 25, 1991, has been disclaimed.

[22] Filed: Apr. 5, 1974

[21] Appl. No.: 458,129

Related U.S. Application Data
[63] Continuation-in-part of Ser. No. 193,494, Oct. 28, 1971, Pat. No. 3,819,742.

[30] Foreign Application Priority Data
Nov. 3, 1970 France .............................. 70.39537

[52] U.S. Cl. .................. 208/308; 55/16; 260/674 R
[51] Int. Cl.² ...................... B01D 13/00; C07C 7/00
[58] Field of Search ......... 260/681.5, 677 A, 674 R; 208/308; 210/23, 23 H, 23 U; 55/16, 158

[56] References Cited
UNITED STATES PATENTS

| | | | |
|---|---|---|---|
| 2,159,434 | 5/1939 | Frey ................................ | 260/677 A |
| 2,475,990 | 7/1949 | Robertson ....................... | 260/676 R |
| 2,947,687 | 8/1960 | Lee .................................... | 208/308 |
| 2,960,462 | 11/1960 | Lee et al. ............................ | 208/308 |
| 2,981,680 | 4/1961 | Binning ................................ | 210/23 |
| 3,370,102 | 2/1968 | Carpenter et al. ............... | 260/674 R |
| 3,563,889 | 2/1971 | Cooper et al. ....................... | 210/23 |
| 3,819,742 | 6/1974 | Brun et al. ........................... | 208/308 |

Primary Examiner—Herbert Levine
Attorney, Agent, or Firm—Hammond & Littell

[57] ABSTRACT

The invention relates to a process for separating mixtures of hydrocarbons, notably conjugated diene hydrocarbons or aromatic hydrocarbons, from mixtures containing the same, by the general technique of permeation or pervaporation through specific membranes.

The specific membranes used are formed of a high polymer comprising functional groups chemically combined by covalent bonding within the polymer forming the said membrane, the said groups possessing a physicochemical affinity, notably a capacity to complex, with respect to one of said hydrocarbons and, substantially, the absence of such a capacity with respect to other hydrocarbons of the mixture. For the separation of dienes, such as butadiene and pentadiene, membranes are used containing active nitrile, pyrrolidone, N-substituted groups, such as N-alkyl groups, preferably N-vinyl or N-methyl-pyrrolidone. The membrane can be obtained, for example, by copolymerization of butadiene with acrylonitrile, with the membrane containing about 2.5% to 30% of active nitrile groups and preferably from 15% to 20%.

53 Claims, 4 Drawing Figures

PROCESS FOR SEPARATING HYDROCARBONS

PRIOR APPLICATION

This application is a continuation-in-part of our co-pending, commonly assigned application Ser. No. 193,494 filed Oct. 28, 1971, now U.S. Pat. No. 3,819,742.

STATE OF THE ART

The known processes for the industrial separation of hydrocarbons usually make use of the technique of liquid-liquid extraction or extractive distillation. In liquid-liquid extraction, for instance, sulfuric acid is used to extract the isobutene from a cut of $C_4$ hydrocarbons already previously depleted of butadiene. The sulfuric acid in fact permits selective dissolving of the isobutene from the $C_4$ hydrocarbon mixtures. An example of extractive distillation is that of the separation of dienes in cuts of $C_4$ and $C_5$ hydrocarbons, the butadiene being separated from the $C_4$ cut and the 1-3 pentadiene from the $C_5$ cut. In this case, acetonitrile is used as a selective solvent. The petroleum industry also uses N-methyl-pyrrolidone as a solvent for the extraction of butadiene and pentadienes.

The drawback to said known separation processes is that their yield decreases in proportion as the extraction or distillation evolves. Furthermore, they imply the use of bulky installations and large equipment, and are therefore costly. The cost of maintaining said units is also high.

Efforts have already been made in the prior art to overcome these various drawbacks by passing the mixture of hydrocarbons to be separated over porous substrates containing a selective extraction solvent. As an illustration, U.S. Pat. No. 3,244,763 proposes stripping the isobutene from a $C_4$ hydrocarbon cut by passing the hydrocarbon mixture across a porous substrate impregnated with sulfuric acid. The isobutene is pumped through said substrate owing to the action of the sulfuric acid which is secured thereto. The isobutene can thus be removed from the other side of the wall of the porous substrate, by a solvent such as hexane.

Similarly, United Kingdom Patent No. 1.090,096 suggests a separation treatment which, instead of being applied to hydrocarbons employs hydrometallurgical compounds. More particularly, it deals with the separation of uranyl nitrate from solutions also containing iron nitrate and aluminum nitrate. To carry out separation, the solutions are flowed over a porous support on which there is deposited a coat of polyvinyl chloride plasticized with a tributyl phosphate or by other phosphoric esters.

In the examples illustrating the prior art which have been mentioned, the selective solvent is only physically integral with the porous support. This is exactly the case of a support impregnated with sulfuric acid. It is the same thing when the porous support is coated with polyvinyl chloride plasticized with tributyl phosphate, which acts as a solvent. In polyvinyl chloride, as a matter of fact, the tributyl phosphate forms a simple physical, though intimate, mixture with the macromolecules of the vinyl chloride polymer. The plasticizer is not, however, chemically bonded to the macromolecule.

In other cases, it has been suggested that membranes without electrical charges should be used to separate metallic ions. Such membranes carry functional groups adapted to the nature of the ions to be separated. Said separation techniques are illustrated by U.S. Pat. Nos. 3,450,630 and 3,450,631 and obviously do not apply to the separation of hydrocarbon mixtures.

Other problems arose with the separation of mixtures of aromatic and aliphatic hydrocarbons. In the $C_6 - C_8$ oil cuts, the aromatic hydrocarbons are, in the majority of cases separated from the aliphatic hydrocarbons by extractive distillation. However, the solvents cannot be used if the boiling point is lower or equal to the middle boiling temperature of the mixture to be separated. Thus the separation of benzene from heptane, for example, cannot be contemplated in extractive distillation with acetonitrile even though studies of solubility state a good power of theoretical separation (partial immiscibility of the heptane in the acetonitrile and total miscibility of the benzene in acetonitrile).

Other documents embodying the state of the art will also be studied in detail hereinafter.

U.S. Pat. No. 2,388,095 relates to a process for refining mineral oils particularly in order to separate iso-olefins from mixtures thereof with normal olefins. The mixtures of gas to be treated is introduced into a high-pressure compartment separated from a low-pressure compartment by a membrane which is maintained on a perforated metal plate. Gas fractions enriched with one or the other components of the mixture are collected on either side of the membrane. The description of U.S. Pat. No. 2,388,095 mentions that the use of rubber membranes as solid solvents to separate hydrocarbon gases from unsaturated hydrocarbon gases is known. The comparative example given in the patent shows that separation with such a rubber membrane is not satisfactory. U.S. Pat. No. 2,388,095 suggests other types of solid solvents, notably membranes obtained by the polymerization of isobutylene or by the copolymerization of an iso-olefin such as isobutylene with a conjugated diolefin. Such membranes act as solid solvents with respect to iso-olefins and are therefore unsuitable for separating conjugated diene hydrocarbons from the hydrocarbon mixture containing them. This patent also teaches that rubber membranes are not satisfactory. Furthermore, the process of U.S. Pat. No. 2,388,095 is only applicable to the separation of gaseous mixtures.

United Kingdom Patent 1,069,231 relates to a process for separating fluid or gaseous mixtures, and notably an improved apparatus for carrying out said process. The technique used depends on the phenomenon of permeation or pervaporation already described in the literature (see U.S. Pat. Nos. 2,540,151 and 2,540,152) wherein one of the constituents of the mixture to be separated dissolves in the membrane and migrates through the latter under the influence of a pressure or concentration gradient.

United Kingdom Patent 1,069,231 is an example of prior art which illustrates the practical application of such a technique. The object of this patent is an apparatus permitting a large, active membrane surface area per unit volume and defines the technological parameters (pressure, thickness of the membrane, etc.) providing the best results. The indications relate neither to the nature of the membranes used nor to that of the mixtures separated. Moreover, the specific examples of United Kingdom Patent 1,069,231 relate to the purification of sea-water, organic products or the separation of carbon dioxide from certain mixtures. United Kingdom Patent 1,069,231 does not, therefore, teach means adapted to separate hydrocarbons, and it does not define the membranes which could be suitable for such an application.

French Patent 1,371,343, with its addition Patents 72,416, 72,867 and 72,899, as well as French Patent 1,568,217, relate to semi-permeable membranes, which contain active groups grafted into the mass. Said groups can be acid or basic groups, such as carboxylic acid groups, or originating in a basic monomer of the pyridine or amine type. Such membranes can be used for ion exchanges in the techniques of electrodialysis or reverse osmosis. Furthermore, their chemical structure is peculiar, as their skeleton consists of a perhalogenated polyolefin.

The various aforesaid French patents do not therefore describe membranes which can be used for the separation of mixtures of hydrocarbons.

U.S. Pat. No. 3,225,107 concerns, generally speaking, a process for separating organic compounds in the form of a liquid mixture by a permeation technique using a polymeric membrane onto the surface of which another polymer has been grafted. Said grafting can be carried out on one and/or the other surface of the membranes, but in any case, as is mentioned in the specification and illustrated in the drawings of said U.S. Pat. No. 3,225,107, it concerns membranes consisting of a thick, permeable support and a thin film applied to the surface thereof which provides selective separation.

Said surface grafting is effected by the polymerization of an active monomer according to conventional grafting techniques. When the support has a thickness of from 12.5 to 25 microns, the film grafted on the surface is no thicker than 2.5 microns. The constitution of the membrane is therefore heterogenous inasmuch as the molecules of the component to be separated first come into contact with the grafted film, then pass through a thick layer of inert, porous material before arriving at the other side of the membrane, having optionally passed through another grafted film if grafting has been effected on both sides of the membrane. Such heterogeneity is an obstacle to the use of such membranes for the separation of certain gaseous or liquid mixtures. In certain cases, in fact, the component to be separated can in actual fact dissolve in the surface grafted film, but it is then stopped by the thick support layer whereby separation cannot take place. If the support layer is porous, the separation level remains insufficient and the overall yield of the operation is low. Finally, U.S. Pat. No. 3,225,107 vaguely mentions the application of the process of the separation of various mixtures of hydrocarbons, but it does not teach the means for separating conjugated diene hydrocarbons from mixtures containing same.

Other prior art describing the general technique of permeation are U.S. Pat. Nos. 2,953,502 and 2,981,680. The first is limited to the separation of azeotropic mixtures. The second relates to the separation of various mixtures and has as an object a process using two different types of membranes selective with respect to certain components of the mixture. The apparatus for carrying out said process is described in detail. The process is especially applicable to the separation of azeotropic mixtures, such as water and pyridine. Fractionation of mixtures of hydrocarbons and those containing conjugated diene hydrocarbons is not contemplated in said last patents.

OBJECTS OF THE INVENTION

It is an object of the present invention to provide a process for the separation of mixtures of hydrocarbons, which does away with the drawbacks of the above-described prior art techniques of selective extraction by solvents and extractive distillation, and which makes use of specific polymer membranes applying the general technique of permeation or pervaporation.

It is another object of the present invention to more particularly provide a process for the separation of conjugated diene hydrocarbons from mixtures also containing saturated hydrocarbons or olefin hydrocarbons.

It is a particular object of the present invention to provide a process for the separation of butadiene from the isobutene in a petroleum cut of $C_4$ hydrocarbons.

It is another object of the present invention to provide a process for the separation of isoprene and pentadienes.

It is still another object of the present invention to provide a process for the separation of isobutene from a mixture containing isobutene and 1-butene.

It is a further object of the present invention to provide a process for the separation of mixtures of aromatic and aliphatic hydrocarbons such as mixtures of benzene and heptane.

Another object of the invention is to provide a process for the separation of a mixture of hydrocarbons, particularly conjugated diene hydrocarbons, from mixtures containing the same, by the general technique of permeation and pervaporation through an improved membrane, characterized in that the said mixture is contacted with a membrane formed of a high molecular weight polymer comprising functional active groups chemically combined by covalent bonding within the polymer of which the said membrane is made, the said groups having a physicochemical affinity, notably a capacity to complex with respect to one of said hydrocarbons and, substantially, the absence of such a capacity with respect to other hydrocarbons of the mixture, and that a pressure gradient or chemical potential is applied to the said improved membrane in a known manner, which permits the recovery, on either side of the membrane, of a fraction enriched by the hydrocarbon having selectively passed through the membrane, and a fraction containing, predominantly, the other hydrocarbons of the mixture.

These and other, further objects of the present invention will become apparent as the description thereof proceeds.

DESCRIPTION OF THE INVENTION

The present invention relates to the field of the separation of mixtures of hydrocarbons. The invention relates more particularly to the separation of conjugated diene hydrocarbons from mixtures also containing saturated or olefinic hydrocarbons. The invention further relates to the separation of mixtures of olefin isomers, as well as relating to the separation of mixtures of aromatic and aliphatic hydrocarbons.

More particularly, the present invention is directed to an improvement in the process for separating hydrocarbons from mixtures thereof of hydrocarbons with similar boiling points by permeation or pervaporation through a specific membrane, wherein the improvement consisting of contacting a mixture of hydrocarbons with similar boiling points with a membrane formed of a high molecular weight polymer containing functional groups chemically combined by covalent bonding within the polymer forming the said membrane, the said groups possessing a physicochemical affinity, with respect to one of said hydrocarbons and substantially the absence of such an affinity with respect to other hydrocarbons of the mixture; the membrane used being substituted with an active group selected from the group consisting of nitrile, pyrrolidone, β-lactam, N-substituted groups, and sulfonic acid functional groups; and applying a gradient of pressure or chemical potential to the said membrane whereby on one side of the membrane a fraction enriched with the hydrocarbon having selectively passed through the membrane, and on the other side of the membrane a fraction containing predominantly the other hydrocarbons of the mixture are obtained.

Preferably the present invention provides an improved process for separating from hydrocarbon mixtures containing a specific hydrocarbon to be separated, the following specific hydrocarbons and mixtures: butadiene to be separated from a mixture containing butadiene and isobutene optionally mixed with other hydrocarbons, pentadienes to be separated from a mixture containing pentadienes and isoprene, isobutene to be separated from a mixture containing isobutene and 1-butene, benzene to be separated from a mixture containing benzene and heptane. The mixtures containing isobutene and 1-butene preferably consist of only these two compounds in which there is from 50% to 70% by volume of isobutene and 30% to 50% by volume of 1-butene. The mixtures containing benzene and heptane preferably consist of (A) a mixture consisting of 20% to 88% of benzene and 12% to 80% of heptane or of (B) 1% to 20% of benzene and 80% to 99% of heptane.

The new specific membranes used in the process of the invention can be formed by chemical modification of a wellknown basis polymer which is a plastic material or an elastomer. Polystyrene, polyethylene, polyvinyl chloride or polytetrafluoroethylene ("Teflon") can, for example, be used as a plastic material. Preference is generally given to elastomer membranes owing to the fact that the macromolecular chains are more mobile and higher coefficients of diffusion are thus obtained. The starting materials for such elastomers are natural and synthetic rubbers, such as, among others, copolymers of ethylene and propylene, butyl rubber, polyisoprenes, polybutadienes, and polyoxypropylene.

The aforesaid polymers are used in the form of a membrane, that is to say, a thin film. In practice, membranes of a thickness of one thousandth of a millimeter to 0.5 millimeter are suitable. Theoretically, thicker membranes can be used, but they provide lower separation rates. To obtain the best results, a minimum thickness is used, compatible with mechanical strength and long life. It is usual to apply the membrane to a porous support, which contributes to the mechanical strength of the whole. The membrane itself is not, therefore, subjected to mechanical stresses and it can be very thin, for example, one micron.

The conventional techniques for preparing such membranes from crude basis polymer material are known. A first technique consists in molding the polymer material under pressure. It does not permit membranes thinner than about one-tenth of a millimeter to be obtained, but cross-linking or vulcanization can be effected simultaneously in the press. According to a second technique, which is preferred for the requirements of the invention, a polymer solution is prepared in a solvent such as an aromatic hydrocarbon like benzene, chlorinated solvents such as chloroform, chlorinated aromatic hydrocarbons, etc. The solution also usually contains vulcanization ingredients. A form corresponding to the membrane to be manufactured is soaked in the polymer solution, the concentration of which notably permits the thickness of the final membrane to be varied. The form is dried gently to evaporate the solvent, first at ambient temperature, then in an oven at 40°C with nitrogen or another inert gas to prevent oxidation, and finally at temperatures of about 140°C to 160°C. It is essential to evaporate all the solvent and to avoid bubbles in order to obtain a thin, continuous membrane. This known technique enables elastomer membranes one-hundredth of a millimeter thick to be obtained easily. Generally speaking, and in the case of an elastomer membrane, the use of a vulcanized membrane is suitable for the practical embodiment of the invention. The imperative condition is that the basis membrane which does not contain active groups cannot dissolve in the liquid phase of either of the components of the mixture to be separated. Moreover, an elastomer membrane is fragile if it is not vulcanized. In all cases where one of the components is liquid, a vulcanized membrane should be used. The means for cross-linking or vulcanizing the aforesaid polymer are known in themselves. The operation may be effected with sulfur vulcanizing agents, with peroxides or by irradiation.

The preceding observations concern the nature of the basis high polymer used to make the membrane of the invention and the practical modes for embodying it. It is a question of the conditions relating to the substrate of the membrane as the latter should, furthermore, have other characteristics.

In the general definition previously given it was stated that the macromolecules of the polymer have chemically functional groups chemically combined by covalent bonding within the polymer, the said groups having a physicochemical affinity with respect to one of the components of the mixture to be separated, and particularly one of the hydrocarbons. The functional groups have as an essential role to increase the selectivity that a membrane constituted of the same basis polymer without functional groups may have with regard to a certain mixture of hydrocarbons.

Within the meaning of the present invention, the expression "functional groups chemically combined by covalent bonding within the polymer" means that the functional groups are distributed evenly throughout the polymer mass, as opposed to membranes of a support-skeleton with an active film on the surface thereof. In other words, when a membrane according to the invention is used, the molecules of the selectively separated hydrocarbon pass through the membrane and always come into contact with the same composition of material throughout the total thickness of the membrane, the distribution of functional groups being even in the mass throughout the thickness of the membrane.

The functional groups in question can either be fixed chemically by grafting onto the macromolecules of a preexisting high molecular weight polymer, or directly integrated with the skeleton of the macromolecular chains during polymerization with another monomer as is the case with copolymers where one of the monomers has an active functional group.

The following examples are merely illustrative in defining the general concept of physicochemical affinity. In the separation of dienes such as butadiene and pentadiene it is known, from experience with extractive distillation, that certain functional groups can be present in the solvents used to permit selective extraction. Thus, pyrrolidone alone does not permit the dienes to be extracted from $C_4 - C_5$ hydrocarbon cuts, whereas N-methyl-pyrrolidone provides selective extraction of butadiene and pentadienes. The presence of the N-substituted group therefore appears to be connected with the selective capacity of the solvent.

Similarly, the decisive function played by nitrile groups has been noticed when acetonitrile is used as a solvent for the extraction of dienes from $C_4 - C_5$ hydrocarbon mixtures. The acetonitrile acts by increasing the boiling points of said compounds.

In liquid-liquid extraction to separate isobutene, advantage is taken of the property possessed by sulfuric acid to selectively complex isobutene in a $C_4$ hydrocarbon cut depleted of butadiene The active role of sulfuric acid should therefore be noted.

From the above examples, and others, the nature of functional groups which increase the selectivity of a membrane can be foreseen. These functional groups should be the same as those possessed by a liquid organic solvent having a particular affinity with respect to one of the hydrocarbons of the mixture to be separated. This affinity is the result of the formation of an electronic complex characterized by a resonant structure between the solvent molecules and the molecules of the said hydrocarbon.

A practical criterion exists which permits one skilled in the art to examine a posteriori the role of intensifying the selectivity of the active groups. This criterion is that the swelling of a membrane with active groups increases its selectivity towards a given mixture of hydrocarbons. This selectivity is a more effective selectivity than is the selectivity of a membrane with the same basic structure but without active groups. This increase in the swelling of the improved membrane as compared to conventional membranes proves the electronic complex formation between the active groups of the improved membrane and one or several components of the mixture to be separated.

Polymers can be obtained in which the active groups are combined with macromolecules, by being chemically bonded thereto, by the usual techniques such as grafting or copolymerization. For the purpose of the grafting which should take place in the basic polymer mass, the polymer and at least one compound providing active groups are contacted with catalysts containing peroxide or diazoic compounds. Simple heating is sometimes sufficient to obtain said grafting. In the case when, as is preferred, elastomer membranes are used, the membrane should retain its elastomeric properties after the grafting has ended. For copolymerization, the usual techniques are used, employing radical or ionic catalysts or which employ simple heating. Examples of such techniques will be given hereinafter with respect to particular applications of the process of the invention.

It is essential to note that the component selectively separated from the mixture diffuses through the improved membrane, but that after the passage of said component the membrane remains chemically unchanged. It is thought that the molecules of the selectively separated hydrocarbon, whether they be gaseous or liquid, when they are contacted with the membrane, pass through the macromolecules of the membrane in a complexed state, the electronic structure of the selectivity permeating species being different during its diffusion from that of the said species in its normal electronic configuration. When separation is completed the membrane is ready to be reused without further treatment.

A fundamental difference is thus observed compared with certain techniques using exchange resins, or others in which it is compulsory to carry out a regeneration treatment to remove the component, selectively fixed onto this type of resin. Owing to this property, it can also be understood that the process of the invention is perfectly adapted to continuous operation.

Elastomer membranes permit high diffusion coefficients to be obtained, particularly owing to their use at a temperature very much higher than their glass transition point. It should also be noted that following the usual vulcanization treatment, the active groups which are grafted or are part of the polymer macromolecule are not modified.

In order to increase the yield during separation, it may be advantageous to contact the mixture of components in a liquid state. In a liquid phase, the density of the selectively permeating species is very high and the yield of the separated component increases. Owing to the conditions previously specified with respect to the polymer substrate, the polymer skeleton does not prevent migration of the molecules of the component to be separated. It should also be noted that, during transfer of the components through the membrane, two parameters exert an influence, they are, the electronic interactions of the components with the active groups of the improved membrane and the values of the diffusion coefficients through the membrane.

It is understood that the overall action exerted by the membrane on the component to be extracted is the sum of the action of the active groups chemically combined by covalent bonding with the polymer and that of the basis polymer proper. Consequently, the action peculiar to the polymer substrate should be such that it encourages the action of the active groups. Said action can nevertheless be inoperative, or slightly unfavorable.

For the separation of dienes from hydrocarbon mixtures containing the same, a membrane containing nitrile active groups can be used, and particularly a membrane containing a butadiene acrylonitrile-copolymer. The nitrile (CN groups) content of the specific membrane can be in the range of about 2.5 to 30%. It is advantageously from 15 to 20%. Some copolymers of this type are known by the name of "Buna N". Others are put on the market by the Societe Plastimer (France) under the name "Butacryl". A membrane containing butadieneacrylonitrile copolymers has the property of complexing the conjugated dienes owing to the electronic affinity between the nitrile groups and the dienes.

Other active groups for the separation of conjugated dienes are of the N-substituted type or the pyrrolidone type. N-alkyl groups, such as the N-methyl group can be mentioned. Examples of compounds providing such active groups are N-methyl-pyrrolidone, N-vinyl-pyrrolidone and maleic N-methylimide. When said groups are fixed by grafting onto an elastomer, the membrane obtained has the property of selectively extracting butadiene and pentadiene from the hydrocarbons treated. Polymers bearing N-substituted grafted groups, such as N-methyl groups, can be obtained by the usual techniques previously mentioned. As an example, rubbers modified with N-methyl pyrrolidone were described in the Bull.Soc.Chim. 1961, p.1433 by Christian Pinazzi, Jean-Claude Danjard and Rene Pautrat. Such modified rubbers bear a variable number of groups fixed to the molecule, and may notably amount to between 10 and 30% by weight based on the initial polymers. The rubbers obtained are converted into said improved membranes by the solvent evaporation technique previously described. Suitable solvents are chlorinated aromatic solvents and heavy ketones.

N-substituted groups, such as N-alkyl groups or pyrrolidone groups, can also be grafted onto various plastic materials such as polyacrylonitrile (See, for example, Graft Polymers, p. 78 by Battaerd and Tregear, series Polymer reviews No. 16, Interscience Public.1967).

A third category of membrane, which is suitable for the separation of isobutene, is prepared from polymers comprising combined or grafted strong acid groups. An example of such polymers is described in French Patent No. 69,41,159 which relates to a process for the preparation of sulfonated polymers and the products obtained. Elastomer substrates suitable for the manufacture of said sulfonated polymers are polybutadiene and polyisoprene rubbers and ethylene-propylene copolymers. Such sulfonic groups can also be fixed onto plastic materials such as polystyrene, polyethylene and polytetrafluoroethylene ("Teflon"). Fixing on polystyrene is described, for instance, in "Chemical Reactions of Polymers" pp. 280–283 by H. M. Fettes, series High Polymers, Vol. XIX, Interscience Publ. 1964). All the membranes in this category enable isobutene to be separated from a mixture containing isobutene and 1-butene.

In the $C_6$ to $C_8$ oil cuts containing aromatic and aliphatic hydrocarbon mixtures, the aromatic hydrocarbons have been, in the majority of cases, separated from the aliphatic hydrocarbons by extractive distillation. One of the advantages of the process of the present invention is that separation of these mixtures by use of membranes is possible. In fact if a type of active group exists in a solvent which seems, potentially, to be used in extractive distillation, it has been discovered that in many instances said solvent cannot be used if the boiling temperature is lower or equal to the middle boiling temperature of the mixture to be separated. An advantage according to the invention is that the use of membranes bearing active groups obviates this limitation of the prior art process of extractive distillation.

Thus the separation of benzene from heptane is not possible by extractive distillation with acetonitrile, whereas solubility studies predict a good power of theoretical separation (partial immiscibility of the heptane in the acetonitrile and total miscibility of the benzene in acetonitrile). In this regard Example 9 infra demonstrates the novelty of the present process for using these membranes and the improvement brought about by the elastomer membranes including nitrile groups for the separation of aromatic and aliphatic hydrocarbons mixtures.

Another improvement over the prior art consists also in the use of membranes of an elastomeric substrate such as butadiene-styrene copolymers, for the separation of aromatic compounds, said membranes comprising a chemically grafted image of the molecule of which the permeability can be increased through use of the membrane. Example 10 provides an example of a chemically grafted group identical to the molecule which is to be passed through the membrane, and which give to this membrane a physicochemical affinity with respect to the said molecule. These grafts are chemically combined within the polymer forming the membrane, as are the other functional groups used in the process for separating hydrocarbons of the present invention; and they have a physicochemical affinity with respect to one of hydrocarbons of the mixture to be separated. Specifically in Example 10 the phenyl group of the styrene molecule within the butadiene styrene copolymer is identical to the benzene molecules which are selectively to pass through the membrane.

If the mixture of aromatic and aliphatic hydrocarbons consists of from 20% to 88% of benzene and of from 12% to 80% of heptane, then the membrane utilized for the separation consists of a butadiene-acrylonitrile copolymer having from 60% to 80% of butadiene, preferably 70%, and having from 20% to 40% of acrylonitrile, preferably 30% acrylonitrile. If the mixture of aliphatic and aromatic hydrocarbons consists of from 1% to 20% of benzene and from 80% to 99% of heptane, then the membrane utilized for the separation consists of a butadiene-styrene copolymer having from 23.5% to 63.5% of styrene, preferably 53.5% of styrene and having from 36.5% to 76.5% of butadiene, preferably 46.5%, and may be substituted with an active group selected from the group consisting of nitrile, and N-substituted groups.

According to the invention, it is also advisable to apply a gradient such as a pressure gradient or a gradient of chemical potential to the membrane to permit migration of the selectively selected component through the said membrane.

Said chemical potential gradient can notably be obtained by establishing a difference in partial pressure of the component to be separated on either side of the membrane, a difference in concentration of said component or a difference in temperature.

Pressure can advantageously be exerted on the surface of the membrane with which the mixture is in contact, or the vacuum applied to the other surface of the membrane, that is to say, that from which the separated component is collected, or both said means can be applied together. It may also be advisable to use a temperature gradient between the two mediums separated by the membrane. The specific examples hereinafter show, notably, that lowering the temperature enables a higher yield of separated gaseous constituents to be obtained.

One of the devices for carrying out the process of the invention comprises, essentially, an enclosure separated by a membrane into at least two compartments, the said membrane being integral with a flat, conical, or cylindrical porous support, means for introducing the mixture to be separated into one of the compartments and means in the other compartment for withdrawing the separated components, as well as means for applying a pressure gradient on either side of the said membrane.

Thus, in the upstream compartment, the mixture to be separated is caused to reside or circulate at atmospheric pressure, or under pressure, either in the gaseous state or in the liquid state.

In the downstream compartment, the separation product, or permeate, is withdrawn by a gas or liquid carrier or extracted under vacuum. The invention will now be illustrated by reference to the appended drawings in which:

Figure 1:
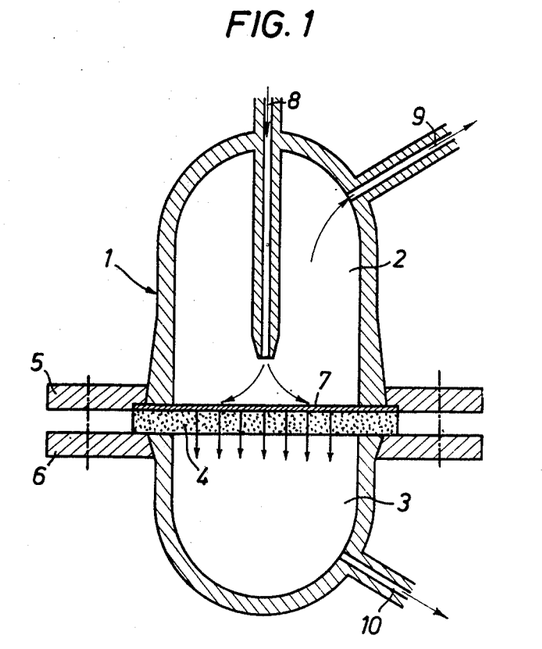
FIG. 1 shows a diagramatic cross sectional view of a device for carrying out the process with a membrane disposed on a porous support.

As can be seen in FIG. 1, the device comprises an enclosure or chamber 1 separated into an upstream compartment 2 and a downstream compartment 3 by a porous support 4 which can be planar, convex or concave. The portions of chamber defining compartments 2 and 3 are maintained by side flanges 5, 6. A membrane 7 is integral with the porous support 4. A pipe 8 entering compartment 2 to supply the mixture to be separated under pressure. Another pipe 9 is used to withdraw the excess mixture from the upstream compartment 2. A pipe 10 is provided in compartment 3 to extract the permeate.

Figure 2:
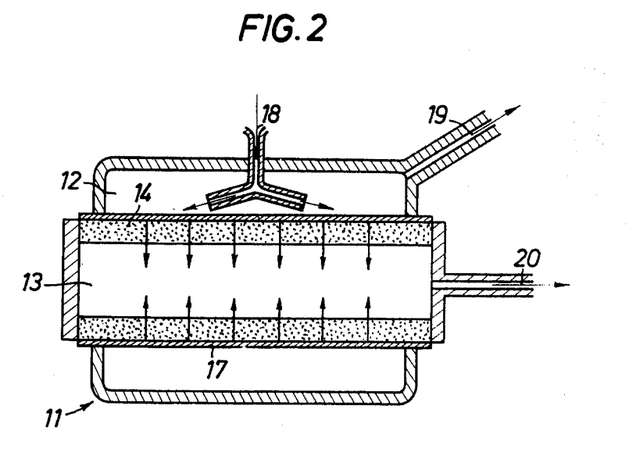
FIG. 2 is another device embodying a membrane integral with a porous, tubular support.

In the device of FIG. 2, chamber 11 is cylindrical in shape. It is separated into an upstream compartment 12 and a downstream compartment 13 by a tubular porous support 14 bearing a membrane 17 about the entire periphery thereof. As is the case in FIG. 1, the mixture to be separated is introduced through pipe 18 and the excess mixture is withdrawn from compartment 12 through pipe 19. Pipe 20 is used to withdraw the permeate from compartment 13.

Figure 3:
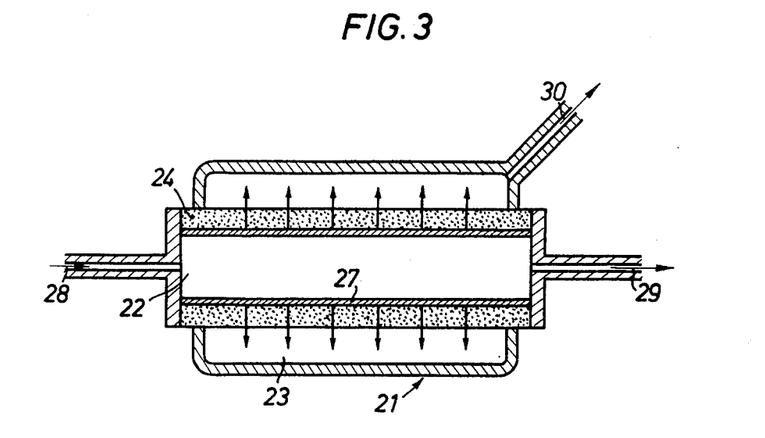
FIG. 3 is a variant of the device of FIG. 2.

FIG. 3 shows a device similar to that of FIG. 2. In this case, chamber 21 is also cylindrical and the porous support 24 is tubular. However, it is the inner surface of tube 24 which is covered by membrane 27. The upstream compartment 22 is situated within the tube and the downstream compartment 23 is outside it. The mixture to be separated is introduced through tube 28 and the excess mixture is withdrawn through pipe 29. The permeate is recovered by means of pipe 30.

The invention will now be illustrated, without being limited by specific examples of embodiment employing the devices shown in the appended drawings.

EXAMPLE 1

A mixture of hydrocarbons consisting essentially of butadiene and isobutene was treated.

Membranes were made with butadiene-acrylonitrile copolymers sold under the name "Butacryl". Product BT 205 is a polymer containing 16.7% nitrile active groups and product BT 305 contains 18.6% nitrile active groups. The vulcanized membranes obtained with these products have the following specific gravity characteristics:

Specific gravity:
  0.98 with type BT 205;
  0.99 with type BT 305

In the crude state the Mooney viscosity is respectively: with
BT 205 = 45 to 55
with
BT 305 = 50 to 55

The vulcanization formulation used was as follows with the parts being by weight:

| Rubber | 100 |
|---|---|
| Zinc oxide | 5 |
| Stearic acid | 2 |
| Sulfur | 1.5 |
| Accelerator (cyclohexyl benzothiazyl-sulfenamide) | 1.5 |

After vulcanization at 153°C for 20 minutes, the obtained membranes possessed the following characteristics:

| With BT 305 | |
|---|---|
| Modulus at 300% elongation | 15.5kg/cm$^2$ |
| Tensile strength | 25 kg/cm$^2$ |
| Elongation (at breaking) | 670% |
| Swelling by volume in toluene (measured at ambient temperature) | 160% |

Vulcanized membranes obtained with BT 205 possessed similar characteristics, with the exception of swelling in toluene, which is 192%.

The membranes used had a thickness of 150$\mu$ in the case of those manufactured with BT 205 rubber, and 300 $\mu$ for those made from BT 305 rubber. As a comparison, membranes were also made of pure polybutadiene containing no acrylonitrile and also having a thickness of 300 $\mu$. After vulcanization, the cross-linking of the membranes was estimated to be about 3.4%.

The device of FIG. 1 was used with a planar, porous support 4 corresponding to the useful surface of membrane 7 equivalent to 38 cm$^2$.

The pressure in the upstream compartment 2 was 2 bars. The pressure in the downstream compartment 3 was 0.1 bar absolute, or 7.6 cm Hg.

The gaseous mixture introduced through pipe 8 contained, by volume 36% butadiene and 64% isobutene.

Using a 300 $\mu$ vulcanized membrane made with BT 305, and at 20°C, a diffusion velocity of butadiene of 0.4 g/h through membrane 7 is measured, with a coefficient of separation of 2.85.

With a conventional rubber membrane containing no nitrile groups, at 20°C a diffusion velocity of 5 g/h is measured, but the coefficient of separation in two independent measurements is 1.02 and 1.01, which shows that there is no effective separation of butadiene taking into account mistakes in measurements.

This example, therefore shows the decisive influence of the presence of nitrile functional groups in the polymer improved membrane. These groups have a structural electronic affinity with respect to butadiene and permitting it to be separated from a butadiene-isobutene mixture.

EXAMPLE 2

Example 1 was repeated, except for the treating of a mixture comprising 75% butadiene and 25% isobutene by volume on a membrane containing a butadiene-acrylonitrile copolymer of the type "Butacryl" BT 205 having a thickness of 150 microns.

The coefficient of separation was measured to be between 2.5 and 3 for the following conditions of pressure:

| Outlet pressure of the permeate | 1 bar |
|---|---|
| Difference in pressure between the upstream compartment and the downstream compartment (pressure gradient) | 0.8 bar |

The useful surface of the membrane was 38 cm$^2$ and the device used was that shown in FIG. 1.

Under these conditions, at a temperature of 17°C, the mixture being introduced in the gaseous state and the downstream compartment flushed with nitrogen to entrain the permeate, the rate of separated butadiene, as measured, corresponded to 2.1 tons per year and per m² of membrane.

By operating at 10°C and using the mixture to be treated in a liquid state, and retaining the sweeping of the downstream compartment with nitrogen, a yield of separated butadiene corresponding to 6.3 tons per year and per m² of membrane was measured.

EXAMPLE 3

This example illustrates the influence of the temperature on the yield of the separated gaseous component.

Example 2 was repeated under identical conditions, except that the temperature was altered. The results obtained are given in Table 1.

TABLE I

The influence of temperature on the yield of separated butadiene.

| Temperature °C | yield g/h membrane surface 38 cm² |
|---|---|
| 5 | — |
| 8 | 3.40 |
| 10 | 3.25 |
| 11 | 2.40 |
| 12 | 2.16 |
| 15 | 1.40 |
| 20 | 0.72 |
| 25 | 0.40 |
| 30 | 0.26 |
| 35 | 0.20 |
| 40 | 0.16 |
| 45 | 0.14 |
| 50 | 0.13 |

Figure 4:
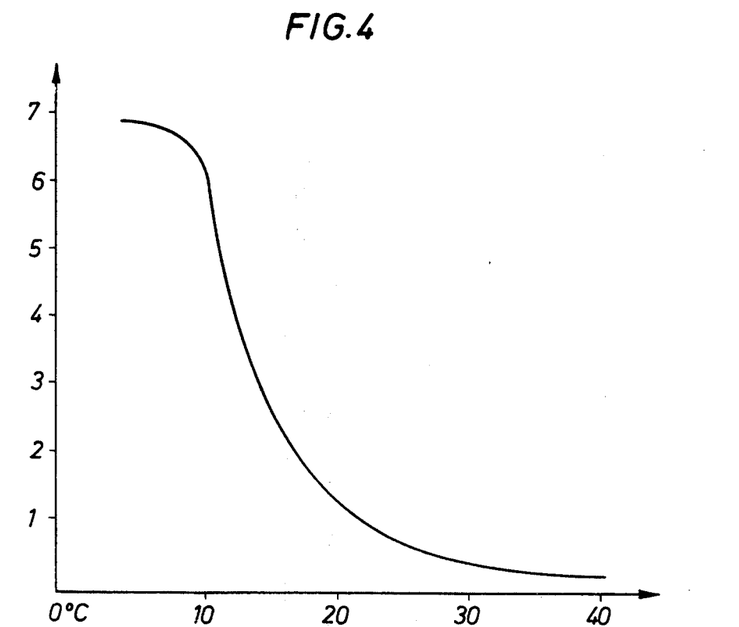
FIG. 4 is a graph showing the influence of the temperature on the separation rate.

FIG. 4 is a graph showing, in abscissa, the temperature in °C and, in ordinates, the separated butadiene yield expressed in tons per year and per m² of the membrane, according to the results given in Table I above.

Thus it can be seen that the yield increased as the temperature decreased. It may, therefore, be advantageous to work at temperatures in the range of about 5° to 20°C.

EXAMPLE 4

To obtain butadiene of a high degree of purity, a mixture containing, by volume, 75% butadiene and 25% isobutene was treated according to the invention in four successive separation stages. Each of the stages being of the type shown in FIG. 1. The characteristics and conditions of treatment were the same as in Example 2.

At the outlet of the 4th separation stage there was obtained a butadiene containing less than 1% impurities.

Equivalent results are obtained by treating the mixture to be separated in a series of devices comprising tubular membranes on porous supports of the type shown in FIGS. 2 and 3.

EXAMPLE 5

In this example, a mixture containing 50% isoprene and 50% cis-trans-1,3-pentadiene by volume was treated.

The device used was the type shown in FIG. 1 with an effective membrane surface of 38 cm². The outlet pressure of the permeate was 0.1 bar and the difference in pressure between the upstream compartment and the downstream compartment (pressure gradient) was 1 bar.

The membrane used contained a butadiene acrylonitrile copolymer of the type Butacryl BT 305 so that the active nitrile groups content of the membrane was 18.6% and the thickness was 150 microns.

Under these conditions there was obtained a coefficient of separation of 2.5 and a yield of 1,3-pentadiene separated at 17°C corresponding to 1 ton/year/m², with the mixture being contacted in the liquid state with the membrane and the separated pentadiene in the gaseous state.

With the same membrane, but of 300 microns, treating the same mixture under an upstream pressure of 1.4 bar and a downstream pressure of 0.1 bar, a coefficient of separation of 2 ± 0.5 and a pentadiene yield of 1.2 g/h at 36°C were obtained.

EXAMPLE 6

In this example, a commercial C₄ cut was treated by pervaporation. The device used was the type shown in FIG. 1, with an effective membrane surface of 44 cm². The outlet pressure of the permeate is 1.0 bar and the difference in pressure between the upstream compartment and the downstream compartment (pressure gradient) is 0.9 bar. The membrane used was made with a butadiene-acrylonitrile copolymer of the BT 305 type, vulcanized with dicumyl peroxide, containing 18.6% active nitrile groups and having a thickness of 16 microns.

The composition of the feed, permeate and the mixture retained on the membrane were reported below in Table II:

TABLE II

| | $C_4$ cut (feed) | Mixture retained | Permeate |
|---|---|---|---|
| ISOBUTANE | 0.6% | 0.7% | 0.2% |
| n-BUTANE | 3.7% | 3.9% | 1.8% |
| 1-BUTENE | 12.6% | 14.1% | 10.0% |
| ISOBUTENE | 33.8% | 35.6% | 21.4% |
| trans-2-BUTENE | 6.3% | 6.4% | 5.8% |
| cis 2-BUTENE | 6.1% | 6.0% | 6.1% |
| BUTADIENE | 36.8% | 33.4% | 54.6% |

Under these conditions, the coefficient of separation of butadiene with respect to isobutene was 2.6 and the yield of permeate is 26.8 g/h, corresponding to a yield of 52 tons/year/m².

EXAMPLE 7

In this example, a mixture containing 50% butadiene and 50% isobutene by volume was treated. The device used was the type shown in FIG. 1 with an effective membrane surface of 44 cm². The outlet pressure of the permeate was 1.0 bar and the difference in pressure between the upstream compartment and the downstream compartment (pressure gradient) was 1.1 bar. The membrane used was a polyisoprene-cis basis polymer grafted in the mass with 9% maleic N-methylimide active groups, and having a thickness of 350 microns.

Under these conditions there was obtained a coefficient of separation of 1.85; and the yield of butadiene separated at 15°C corresponded to 9.9 tons/year/m²; the mixture being contacted in the liquid state with the membrane and the separated butadiene in the gaseous state.

EXAMPLE 8

In this example, a mixture containing 60% isobutene and 40% 1-butene by volume was treated. The device used was the type shown in FIG. 1 with an effective membrane surface of 44 cm$^2$. The outlet pressure of the permeate was 1.0 bar; and the difference in pressure between the upstream compartment and the downstream compartment (pressure gradient) was 1.1 bar. The membrane used was an ethylenepropylene diene monomer (EPDM) basis polymer grafted in the mass by 10% sulfonic acid active groups, and having a thickness of 500 $\mu$.

Under these conditions there was obtained a coefficient of separation of 1.40; and the yield of isobutene separated at 20°C corresponded to 0.50 ton/year/m$^2$; the mixture being contacted in the gaseous state with the membrane and the separated isobutene in the gaseous state.

EXAMPLE 9

The device of FIG. 1 was used with a porous horizontal support providing a useful membrane surface area of 10 cm$^2$. A mixture of hydrocarbons consisting essentially of benzene and heptane (20% to 88% of benzene) was treated. Membranes BT 305 of 150 $\mu$ in thickness were vulcanized for 10 minutes at 165°C with 1% of dicumyl peroxides. These BT 305 membranes were utilized. The values of the coefficients of separation, $\alpha$, and the yields, at 30°C, for the indicated proportions of benzene in the mixture were reported below in Table III:

TABLE III

| % Benzene | $\alpha$ | Yield t/year/m$^2$ |
|---|---|---|
| 20 | 9.5 | 0.28 |
| 50 | 5.2 | 0.76 |
| 88 | 2.1 | 5.8 |

EXAMPLE 10

Example 1 was repeated for the treatment of mixtures of benzene and heptane comprising between 1 to 20% of benzene. The membranes used were butadiene-styrene copolymers comprising 53.5% of styrene, 200 $\mu$ of thickness, useful surface area of 10 cm$^2$, vulcanized for 10 minutes at 165°C with 1.3% of dicumyl peroxide.

The values of the coefficients of separation, $\alpha$, and the yields at 30°C, for the indicated proportions of benzene in the hydrocarbon mixture were reported below in Table IV:

TABLE IV

| % Benzene | $\alpha$ | Yield t/year/m$^2$ |
|---|---|---|
| 1 | 2.6 | 1.5 |
| 9 | 2.45 | 3 |
| 20 | 2.25 | 4.9 |

The invention is not limited to the aforesaid examples of embodiment. It can be applied to very diversified separations and, generally speaking to all mixtures of hydrocarbons which, in the prior art, were separated, or could be separated by liquid-liquid extraction or extractive distillation.

For all said types of separation, the invention teaches the use of improved membranes differing from the conventional ones in the fact that they are made of a high polymer comprising active groups chemically bonded with covalent bonding to macromolecular chains. The said active groups of the membrane having the property of forming electronic complexes with the permeating species, so that they replace the organic phase which forms either the extractant in liquid-liquid extraction operations, or, in the case of extractive distillation, the solvent which raises or lowers the boiling point of the compound to be extracted.

Various modifications of the process of the invention may be made without departing from the spirit or scope thereof and it should be understood that the invention is to be limited only as defined in the appended claims.

We claim:

1. In a process for separating hydrocarbons from mixtures thereof of hydrocarbons with similar boiling points by permeation or pervaporation through a specific membrane, the improvement consisting of contacting a mixture of hydrocarbons with similar boiling points with a membrane formed of a high molecular weight polymer containing functional groups chemically combined by covalent bonding within the polymer forming the said membrane, said high molecular weight polymer being less selective than said functional groups, the said groups possessing a physiochemical affinity, with respect to one of said hydrocarbons and substantially the absence of such an affinity with respect to other hydrocarbons of the mixture; said functional groups being the same as those of a liquid organic solvent having a particular affinity for separating one of the hydrocarbons of the mixture; said affinity resulting from the formation of an electronic complex characterized by a resonant structure between the solvent molecules and the molecules of the said hydrocarbon, which is selectively separated by the specific membrane; the membrane used being substituted with an active group selected from the group consisting of nitrile, pyrrolidone, $\beta$-lactam, N-substituted groups, and sulfonic acid functional groups; and applying a gradient of pressure or chemical potential to the said membrane whereby on one side of the membrane a fraction enriched with the hydrocarbon having selectively passed through the membrane, and on the other side of the membrane a fraction containing predominantly the other hydrocarbons of the mixture are obtained.

2. The process of claim 1, wherein the part of the membrane material which is less selective, is a high plastic polymer selected from the group consisting of polyvinyl chloride, polystyrene, polyethylene and polytetrafluoroethylene.

3. The process of claim 1 wherein the part of the membrane material which is less selective, is an elastomer selected from the group consisting of copolymers of ethylene and propylene, of polyisoprene, of polybutadiene, polyoxypropylene and polyisobutene.

4. The process of claim 1 wherein the membrane has a thickness in the range of between about 1/1000 mm and 0.5 mm.

5. The process of claim 1 wherein the membrane is applied to a porous support.

6. The process of claim 4 wherein a vulcanized membrane is used.

7. The process of claim 1 wherein the specific functional groups used to intensify the separation power are chemically fixed by grafting onto a high polymer in the membrane mass.

8. The process of claim 1 wherein the active functional groups used to intensify the selectivity are directly combined with a basis monomer during a polymerization step.

9. The process of claim 1 wherein the active group improving the separation is an N-alkyl group.

10. The process of claim 9 wherein the said active group improving the separation is the N-methyl group.

11. The process of claim 1 wherein the said active group improving the separation is N-methyl pyrrolidone.

12. The process of claim 1 wherein the specific membrane is obtained by copolymerizing acrylonitrile containing nitrile active groups with butadiene whereby the copolymer contains 5 to 60% of acrylonitrile.

13. The process of claim 1 wherein the specific membrane is obtained in copolymerizing acrylonitrile containing nitrile active groups with butadiene whereby the copolymer contains 30 to 45% of acrylonitrile.

14. The process of claim 3 wherein the specific membrane is vulcanized by curing agents selected from the group consisting of peroxides and sulfur.

15. The process of claim 1 wherein the specific membrane is vulcanized by curing agents selected from the group consisting of peroxides and sulfur.

16. The process of claim 1 wherein said active groups are fixed by grafting into the mass of a basis polymer membrane whereby the copolymer contains 5 to 60% of acrylonitrile.

17. The process of claim 16 wherein the basis polymer is selected from the group consisting of polyvinyl chloride, polystyrene, polyethylene, polypropylene, copolymers of ethylene and propylene, and polytetrafluoroethylene.

18. The process of claim 16 wherein the basis polymer is selected from the group consisting of polyisobutene, polyisoprene, polybutadiene and polyoxypropylene.

19. The process of claim 16 wherein said active groups are selected from the group consisting of N-alkyl and pyrrolidone.

20. The process of claim 19 wherein said active groups are obtained from compounds selected from the group consisting of N-methyl pyrrolidone, N-vinylpyrrolidone and maleic N-methyl imide.

21. The process of claim 1 wherein said acid groups are grafted into the basis polymer membrane.

22. The process of claim 21 wherein the said basis polymer is a rubber selected from the group consisting of polybutadienes, polyisoprenes and ethylene-propylene copolymers.

23. The process of claim 21 wherein the said basis polymer is a plastic material selected from the group consisting of polystyrene, polyethylene and polytetrafluoroethylene.

24. The process of claim 1 wherein pressure is exerted on the surface of the specific membrane with which the mixture to be separated is contacted.

25. The process of claim 1 wherein a vacuum is applied to the surface of the specific membrane opposite to the surface with which the mixture is contacted.

26. The process of claim 1 which is operated at a temperature between about 0°C and 40°C.

27. The process of claim 1 wherein the mixture to be separated is used in the gaseous state.

28. The process of claim 1 wherein the mixture to be separated is used in the liquid state.

29. The process of claim 1 wherein the separated hydrocarbon is separated in the gaseous state.

30. The process of claim 1 wherein the separated hydrocarbon is separated in the liquid state.

31. The process of claim 1 wherein said gradient is a gradient of pressure.

32. The process of claim 1 wherein said gradient is a gradient of chemical potential.

33. In a process for separating hydrocarbons from mixtures thereof containing the same by permeation or pervaporation through a specific membrane, the improvement consisting of contacting a mixture consisting of butadiene or isoprene and a member selected from the group consisting of $C_4$-monoolefins, pentadiene, $C_5$-diolefins and $C_5$-monoolefins with a membrane formed of a high polymer comprising functional groups chemically combined by covalent bonding within the polymer forming the said membrane, the said groups possessing a physiochemical affinity, with respect to one of said dienes or monoolefins and substantially the absence of such an affinity with respect to other dienes and monoolefins of the mixture; the said functional groups are the same as those of a liquid organic solvent having a particular affinity for separating one of the dienes or monoolefins from the mixture; said affinity resulting from the formation of an electronic complex characterized by a resonant structure between the solvent molecules and the molecules of the said diene or monoolefin, which is selectively separated by the specific membrane; the membrane used is substituted with an active group selected from the group consisting of nitrile, pyrrolidone, $\beta$-lactam, N-substituted groups and sulfonic acid functional groups; and applying a gradient of pressure to the said membrane whereby on one side of the membrane a fraction enriched by the diene or having selectively passed through the membrane, and on the other side of the membrane a fraction containing predominantly, the other dienes and monoolefins of the mixture, are obtained.

34. In a process for separating hydrocarbons from mixtures thereof containing the same by permeation or pervaporation through a specific membrane, the improvement consisting of contacting a mixture consisting of butadiene or isoprene and a member selected from the group consisting of $C_4$-monoolefins, pentadiene, $C_5$-diolefins and $C_5$-monoolefins with a membrane formed of a high polymer comprising functional groups chemically combined by covalent bonding within the polymer forming the said membrane, the said groups possessing a physiochemical affinity, with respect to one of said dienes or monoolefins and substantially the absence of such an affinity with respect to other dienes and monoolefins of the mixture; the said functional groups are the same as those of a liquid organic solvent having a particular affinity for separating one of the dienes or monoolefins from the mixture, said affinity resulting from the formation of an electronic complex characterized by a resonant structure between the solvent molecules and the molecules of the said diene or monoolefin, which is selectively separated by the specific membrane; the membrane used is substituted with an active group selected from the group consisting of nitrile, pyrrolidone, $\beta$-lactam, N-substituted groups and sulfonic acid functional groups; and applying a gradient of chemical potential to the said membrane whereby on one side of the membrane a fraction enriched by the diene having selectively passed through the membrane, and on the other side of the membrane a fraction containing predominantly, the other dienes and monoolefins of the mixture, are obtained.

35. The process of claim 34 wherein the active group improving the separation is an N-alkyl group.

36. The process of claim 35 wherein the said active group improving the separation is the N-methyl group.

37. The process of claim 35 wherein the said active group improving the separation is the N-methyl pyrrolidone.

38. The process of claim 35 wherein the specific membrane is obtained by copolymerizing acrylonitrile containing nitrile active groups with butadiene whereby the copolymer contains 5 to 60% of acrylonitrile.

39. The process of claim 34 wherein the specific membrane is obtained in copolymerizing acrylonitrile containing nitrile active groups with butadiene whereby the copolymer contains 30 to 45% of acrylonitrile.

40. The process of claim 38 wherein the specific membrane is vulcanized by curing agents selected from the group consisting of peroxides and sulfur.

41. The process of claim 39 wherein the specific membrane is vulcanized by curing agents selected from the group consisting of peroxides and sulfur.

42. The process of claim 34 wherein said active groups are fixed by grafting into the mass of a basis polymer membrane whereby the copolymer contains 5 to 60% of acrylonitrile.

43. The process of claim 42 wherein the basis polymer is selected from the group consisting of polyvinyl chloride, polystyrene, polyethylene, polypropylene, copolymers of ethylene and propylene, polytetrafluoroethylene, and polyisoprene-cis.

44. The process of claim 42 wherein the initial basis polymer is selected from the group consisting of polyisobutene, polyisoprene, polybutadiene and polyoxypropylene.

45. The process of claim 42 wherein said active groups are selected from the group consisting of N-alkyl and pyrrolidone.

46. The process of claim 45 wherein said active groups are obtained from compounds selected from the group consisting of N-methyl pyrrolidone, N-vinylpyrrolidone and maleic N-methyl imide.

47. In a process for separating hydrocarbons from mixtures thereof containing the same by permeation or pervaporation through a specific membrane, the improvement consisting of contacting a hydrocarbon mixture containing an olefin selected from the group consisting of isobutene and 1-butene with a membrane formed of a high polymer comprising functional groups chemically combined by covalent bonding within the polymer forming the said membrane, the said groups possessing a physiochemical affinity, with respect to one of said olefins and substantially the absence of such an affinity with respect to other hydrocarbons of the mixture; the said functional groups are the same as those of a liquid organic solvent having a particular affinity for separating one of said olefins from the mixture, said affinity resulting from the formation of an electronic complex characterized by a resonant structure between the solvent molecules and the molecules of one of said olefins, which is selectively separated by the specific membrane; the membrane used is substituted with a sulfonic acid active group; and applying a gradient of pressure to the said membrane whereby on one side of the membrane a fraction enriched by the olefin having selectively passed through the membrane, and on the other side of the membrane a fraction containing predominantly, the other hydrocarbons of the mixture, are obtained.

48. The process of claim 47, wherein said hydrocarbon mixture consists of 50% to 70% by volume of isobutene and 30% to 50% by volume of 1-butene.

49. In a process for separating aromatic and aliphatic hydrocarbons from mixtures thereof containing the same by permeation or pervaporation through a specific membrane, the improvement consisting of contacting a mixture comprising from 20% to 88% of benzene and from 12% to 80% of heptane with a membrane formed of a high polymer comprising functional groups chemically combined by covalent bonding within the polymer forming the said membrane, the said groups possessing a physiochemical affinity, with respect to one of said benzene or heptane and substantially the absence of such an affinity with respect to other of said benzene or heptane; the said functional groups are the same as those of a liquid organic solvent having a particular affinity for separating one of said benzene or heptane from the mixture, said affinity resulting from the formation of an electronic complex characterized by a resonant structure between the solvent molecules and the molecules of the said benzene or heptane, which is selectively separated by the specific membrane; the membrane used consisting essentially of a butadiene-acrylonitrile copolymer having from 25% to 50% of acrylonitrile and 50% to 75% of butadiene; and applying a gradient of pressure or chemical potential to the said membrane whereby on one side of the membrane a fraction enriched by benzene or heptane having selectively passed through the membrane, and on the other side of the membrane a fraction containing predominantly, the other one of benzene or heptane, are obtained.

50. The process of claim 49 wherein said membrane contains 30% of acrylonitrile and 70% of butadiene.

51. In a process for separating aromatic and aliphatic hydrocarbons from mixtures thereof containing the same by permeation or pervaporation through a specific membrane, the improvement consisting of contacting a mixture comprising from 0.1% to 20% benzene and 80% to 99.9% heptane with a membrane formed of a high polymer comprising functional groups chemically combined by covalent bonding within the polymer forming the said membrane, the said groups possessing a physiochemical affinity, with respect to one of said benzene or heptane and substantially the absence of such an affinity with respect to other of said benzene or heptane; the said functional groups are the same as those of a liquid organic solvent having a particular affinity for separating one of said benzene or heptane, said affinity resulting from the formation of an electronic complex characterized by a resonant structure between the solvent molecules and the molecules of the said benzene or heptane, which is selectively separated by the specific membrane; the membrane used consisting essentially of a butadiene-styrene copolymer having from 23.5% to 63.5% of styrene and 36.5% to 76.5% of butadiene, and said membrane may be substituted with an active group selected from the group consisting of nitrile, and N-substituted groups; and applying a gradient of pressure or chemical potential to the said membrane whereby on one side of the membrane a fraction enriched by the benzene or heptane having selectively passed through the membrane, and on the other side of the membrane a fraction containing predominantly, the other one of said benzene or heptane, are obtained.

52. The process of claim 51 wherein said membrane contains 53.5% of styrene and 46.5% of butadiene.

53. In a process for separating hydrocarbons from mixtures thereof of hydrocarbons with similar boiling points by permeation or pervaporation through a specific membrane, the improvement consisting of contacting a mixture of aromatic and aliphatic hydrocarbons with similar boiling points with a membrane formed of a high molecular weight polymer containing functional groups chemically combined by covalent bonding within the polymer forming the said membrane, the said groups possessing a physiochemical affinity, with respect to one of said hydrocarbons and substantially the absence of such an affinity with respect to other hydrocarbons of the mixture; the membrane used being substituted with an active group identical to the molecule which is to be passed through the membrane; and applying a gradient of pressure or chemical potential to the said membrane whereby on one side of the membrane a fraction enriched with the hydrocarbon having selectively passed through the membrane, and on the other side of the membrane a fraction containing predominantly the other hydrocarbons of the mixture are obtained.

* * * * *